(12) United States Patent
Yoda et al.

(10) Patent No.: US 8,929,174 B2
(45) Date of Patent: Jan. 6, 2015

(54) ACOUSTIC WAVE IMAGING APPARATUS AND ACOUSTIC WAVE IMAGING METHOD

(75) Inventors: Haruo Yoda, Nishitama-gun (JP); Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 203 days.

(21) Appl. No.: 13/578,002

(22) PCT Filed: Mar. 28, 2011

(86) PCT No.: PCT/JP2011/001823
§ 371 (c)(1),
(2), (4) Date: Aug. 9, 2012

(87) PCT Pub. No.: WO2011/129061
PCT Pub. Date: Oct. 20, 2011

(65) Prior Publication Data
US 2012/0314534 A1      Dec. 13, 2012

(30) Foreign Application Priority Data

Apr. 12, 2010   (JP) .................................. 2010-091290

(51) Int. Cl.
| | |
|---|---|
| *G03B 42/06* | (2006.01) |
| *G01N 29/24* | (2006.01) |
| *G01N 21/17* | (2006.01) |
| *G01N 29/06* | (2006.01) |
| *G01S 7/52* | (2006.01) |

(52) U.S. Cl.
CPC ........ *G01N 21/1702* (2013.01); *G01N 29/0654* (2013.01); *G01N 29/2418* (2013.01); *G01S 7/52046* (2013.01); *G01N 2291/044* (2013.01); *G01N 2291/106* (2013.01)
USPC ........................................................ 367/11

(58) Field of Classification Search
CPC .......... G01N 21/1702; G01N 29/0654; G01N 29/2418; G01N 2291/044; G01N 2291/106; G01S 7/52046
USPC ...................................................... 367/7, 11
See application file for complete search history.

(56) References Cited

U.S. PATENT DOCUMENTS 5,793,703 A * 8/1998 Shippey ............................ 367/7
6,638,228 B1 10/2003 Brock-Fisher et al. ....... 600/443
(Continued)

FOREIGN PATENT DOCUMENTS

| CN | 101213438 | 7/2008 |
|---|---|---|
| JP | 2648110 | 8/1997 |

OTHER PUBLICATIONS

Office Action issued on Mar. 31, 2014, in counterpart Chinese patent application 2001180018266.3, with translation.

(Continued)

*Primary Examiner* — Daniel Pihulic
(74) *Attorney, Agent, or Firm* — Fitzpatrick, Cella, Harper & Scinto

(57) ABSTRACT

An acoustic wave imaging apparatus has a phase aligning unit, which aligns phases of received signals obtained by a plurality of acoustic wave receiving elements. A complex signal acquiring unit generates complex signals out of the phase aligned received signals, and a correlation matrix calculating unit calculates a correlation matrix of the complex signals. An electric power calculating unit calculates constrained minimum power of the received signals, using the correlation matrix and a predetermined constraint vector. The correlation matrix calculating unit calculates the correlation matrix at a predetermined cycle, and sequentially outputs the calculated correlation matrix to the electric power calculating unit at a predetermined cycle, and the electric power calculating unit calculates a plurality of constrained minimum powers in parallel using the calculated correlation matrices, the plurality of constrained minimum powers corresponding to the correlation matrices respectively.

9 Claims, 20 Drawing Sheets

(56) References Cited

U.S. PATENT DOCUMENTS

| | | | |
|---|---|---|---|
| 2003/0065262 A1 | 4/2003 | Stergiopoulos et al. | 600/437 |
| 2003/0204142 A1 | 10/2003 | Brock-Fisher et al. | 600/458 |
| 2008/0196477 A1 | 8/2008 | Van Herpen | 73/24.02 |
| 2009/0299185 A1 | 12/2009 | Oikawa et al. | 600/447 |
| 2011/0083511 A1 | 4/2011 | Taki et al. | 73/602 |
| 2011/0128816 A1 | 6/2011 | Baba et al. | 367/11 |
| 2011/0208035 A1 | 8/2011 | Baba et al. | 600/407 |
| 2011/0307181 A1 | 12/2011 | Nagae | 702/19 |
| 2012/0044785 A1 | 2/2012 | Yoda et al. | 367/92 |
| 2012/0259198 A1 | 10/2012 | Nagae et al. | 600/407 |
| 2012/0281902 A1 | 11/2012 | Oikawa et al. | 382/131 |
| 2012/0314534 A1* | 12/2012 | Yoda et al. | 367/7 |

OTHER PUBLICATIONS

J-F Synnevåg et al., "Adaptive Beamforming Applied to Medical Ultrasound Imaging", *IEEE Transactions on Ultrasonics, Ferroelectrics and Frequency Control*, vol. 54, No. 8, pp. 1606-1613 (Aug. 2007), XP011190325.

M. Karkooti et al., "FPGA Implementation of Matrix Inversion Using QRD-RLS Algorithm", *Asilomar Conference on Signals, Systems and Computers*, pp. 1625-1629 (Oct. 2005).

J-F Synnevåg et al., "Benefits of Minimum-Variance Beamforming in Medical Ultrasound Imaging", *IEEE Transactions on Ultrasonics, Ferroelectrics and Frequency Control*, vol. 56, No. 9, pp. 1868-1879 (Sep. 2009), XP011283394.

C. Dick et al., "Implementing a Real-Time Beamformer on an FPGA Platform", *Xcell Journal*, Second Quarter, pp. 36-40 ($2^{nd}$ Quarter 2007), XP002538192, [online] URL: http://www.xilinx.com/publications/xcellonline/xcell_60/xc_pdf/p36-40_60-beam.pdf>.

T. Asai et al., "A Systolic Array RLS Processor", *2000 IEEE $51^{st}$ Vehicular Technology Conference Proceedings, 2000VTC*, vol. 3, pp. 2247-2251 (May 18, 2000).

JPO Office Action issued on Jun. 10, 2014 in counterpart Japanese patent application 2010-091290, with translation.

* cited by examiner

ACOUSTIC WAVE IMAGING APPARATUS AND ACOUSTIC WAVE IMAGING METHOD

TECHNICAL FIELD

The present invention relates to an acoustic wave imaging apparatus and an acoustic wave imaging method.

BACKGROUND ART

An acoustic wave imaging apparatus (ultrasound wave imaging apparatus, in a case of using an ultrasound wave) which generates a three-dimensional structural image inside an object using an acoustic wave, such as an ultrasound wave, is widely used in medical fields as an inexpensive medical image diagnostic apparatus which produces few side effects. The performance of medical image diagnostic apparatuses improves every year due to improvements in acoustic wave imaging technology. As one technology which further improves performance, an image reconstruction technology using a CMP (Constrained Minimization of Power) method is under research.

The CMP method is a signal processing technology developed as an adaptive antenna technology. The CMP method is a reception method which adaptively adjusts the directivity of reception under a constraint such that the receive gain of a radio wave coming from a desired direction is kept constant, so as to constantly minimize the power of all the received signals, including any interfering waves. According to this method, signals with a good SN ratio can be received, since the ratio of power of any interfering waves to that of desired wave can be minimized.

Adaptive antenna technology is based on the assumption that an array antenna constituted by a plurality of receiving elements is used, and the concrete calculation of the CMP method is generally as follows.

It is assumed that the received signals of n number of receiving elements of an array antenna are x[k, t] (k=1, 2, ..., n) in a complex signal form.

It is assumed that the weights of n of complex numbers are w[k] (k=1, 2, ..., n).

In this case, the output s[t] of the array antenna can be given by Expression (1):

[Math. 1]

$$s[t] = \sum_{k} w[k]^* \cdot x[k, t] \quad (1)$$

Instantaneously received power p[t] is given by Expression (2), in which an asterisk (*) at the right shoulder of a variable identifies a complex conjugate:

[Math. 2]

$$p[t] = \frac{1}{2} \cdot \left| \sum_{k} w[k]^* \cdot x[k, t] \right|^2 \quad (2)$$

If the received power P used for the CMP method is defined as an integration value of the instantaneously received power p[t] within a predetermined time, the received power P is given by Expression (3) in vector form:

[Math. 3]

$$\begin{aligned} P &= \sum_{t} p[t] \\ &= \frac{1}{2} \cdot \sum_{t} \left| \sum_{k} w[k]^* \cdot x[k, t] \right|^2 \\ &= \frac{1}{2} \cdot \sum_{k1} \sum_{k2} \left( w[k2]^* \cdot \left( \sum_{t} x[k2, t] \cdot x[k1, t]^* \right) \cdot w[k1] \right) \\ &= \frac{1}{2} \cdot W^H A W \end{aligned} \quad (3)$$

In Expression (3), W is a weight vector, and is given by Expression (4):

[Math. 4]

$$W = \begin{bmatrix} w[1] \\ w[2] \\ \vdots \\ w[n] \end{bmatrix} \quad (4)$$

A is a correlation matrix of an input signal, and is given by Expression (5):

[Math. 5]

$$A = \sum_{t} \begin{bmatrix} x[1, t] \cdot x[1, t]^* & x[1, t] \cdot x[2, t]^* & \cdots & x[1, t] \cdot x[n, t]^* \\ x[2, t] \cdot x[1, t]^* & x[2, t] \cdot x[2, t]^* & \cdots & x[2, t] \cdot x[n, t]^* \\ \vdots & \vdots & \ddots & \vdots \\ x[n, t] \cdot x[1, t]^* & x[n, t] \cdot x[2, t]^* & \cdots & x[n, t] \cdot x[n, t]^* \end{bmatrix} \quad (5)$$

On the other hand, it is known that the constraint of the CMP method, that the signal gain from a desired direction is constant, can be given by Expression (6) using a constraint vector C which corresponds to the desired direction:

[Math. 6]

$$C^H W = 1 \quad (6)$$

Here the superscript "H" on the right shoulder of the variable identifies the complex conjugate of the transpose of the matrix. Therefore if a weight vector $W_{min}$, which minimizes the received power P in Expression (3), is calculated using Expression (6) as the constraint, and the calculated weight vector $W_{min}$ is substituted into Expression (1), then a received signal of the array antenna based on the CMP method can be calculated. In actual calculation, the weight vector $W_{min}$ is obtained as Expression (7):

[Math. 7]

$$W_{min} = \frac{A^{-1}C}{C^H A^{-1} C} \quad (7)$$

The minimum received power $P_{min}$ is obtained as Expression (8):

[Math. 8]

$$P_{min} = \frac{1}{C^H A^{-1} C} \quad (8)$$

In other words, to calculate a received signal of the array antenna using the CMP method, the following [1] to [3] are sequentially executed:

[1] The correlation matrix A of Expression (5) is calculated using the input signal $x[k, t]$.

[2] The weight coefficient vector $W_{min}$ in Expression (7) is calculated using the constraint vector C and the correlation matrix A.

[3] The received signal in Expression (2) is calculated using the weight coefficient vector $W_{min}$ and the input signal $x[k, t]$.

If only the power of the received signals is required as a received signal, the minimum power $P_{min}$ calculated by Expression (8) is simply used as the received signal. Then a signal having a good SN ratio is obtained with minimum influence of any interfering waves.

Non-patent Literature 1 (NPL 1) reports an example of applying the CMP method to ultrasound echo image processing. The ultrasound echo image processing is processing for generating an image of a structure inside an object by irradiating an object with an ultrasound beam, and receiving ultrasound waves reflected inside the object by a plurality of receiving elements arrayed one-dimensionally or two-dimensionally. If a probe constituted by the plurality of receiving elements is regarded as an array antenna and the CMP method is applied to the processing of received signals, then an improvement in performance of the ultrasound echo image processing can be expected.

CITATION LIST

Non-Patent Literature

[NPL 1]
J. F. Synnevåg et al., "Adaptive Beamforming Applied to Medical Ultrasound Imaging", *IEEE Transactions in Ultrasound, Ferroelectrics, and Frequency Control*, Vol. 54, No. 8, August 2007
[NPL 2]
M. Karkooti et al., "FPGA Implementation of Matrix Inversion Using QRD-RLS Algorithm", *Asilomar Conference on Signals, Systems, and Computers*, Oct. 2005, Pages 1625-1629.

SUMMARY OF INVENTION

Technical Problem

Problems in the case of applying the CMP method, which is an array antenna technology, to the ultrasound echo image processing, as shown in NPL 1, will be described.

A first problem is that the desired wave received by the array antenna is a plane wave coming from a point at infinity, whereas the ultrasound echo signal is a spherical wave from a point at a short distance, and the position where the echo signal is generated changes to a more distant point as time elapses. To solve this problem, in NPL 1, phase aligning delay processing is performed for aligning the phase of the received signal of each receiving element, before the calculation of the CMP method is performed.

A second problem is that the intensity and direction of an interfering wave included in the ultrasound echo signal rapidly changes as time elapses. To solve this problem, in NPL 1, the calculation of the CMP method is repeated at an extremely short cycle.

The CMP method, which includes an inverse matrix calculation processing of the correlation matrix, is by nature a method requiring a high volume of calculation processing. If this CMP method is applied to ultrasound echo signal processing, the calculations involved in the CMP method must be repeated at an extremely short cycle, as mentioned above, and the calculation volume becomes enormous as compared with the case of applying this method to an array antenna.

For a calculation circuit which executes inverse matrix calculation at high-speed, Non-patent Literature 2 (NPL 2), for example, discloses an example of an inverse matrix calculating circuit for application to an array antenna. According to the method disclosed in NPL 2, inverse matrix calculation for a 4*4 matrix can be repeatedly executed at a 0.13 MHz cycle using a floating point type algebraic calculating circuit.

On the other hand, in the case of ultrasound echo image processing, calculation must be performed with at least a 5 MHz or higher cyclic frequency in order to implement the resolution required for echo images. The correlation matrix must be at least a 6*6 to 8*8 size matrix. Since the calculation volume of an inverse matrix is generally in proportion to the cube of the matrix size, this means that 130 to 300 times the calculation speed, as compared with the conventional method, is required to calculate the inverse matrix needed for ultrasound wave echo image processing, which means that the conventional method cannot be used.

NPL 1 however discloses nothing on a method of implementing this enormous calculation volume of the CMP method, including the inverse matrix calculating, using a speed and apparatus scale required for practical commercial use.

As mentioned above, if the CMP method is applied to ultrasound wave imaging processing, then improvement of the contrast and resolution of the ultrasound image can be expected. The calculation procedure for this is also known. But in order to apply the CMP method to regular medical diagnostic apparatuses, enormous numerical calculation processing must be performed at high-speed, and achieving this for practical use is difficult in terms of apparatus scale and processing speed.

With the foregoing in view, it is an object of the present invention to provide a technology for processing calculations based on the CMP method at high-speed in the acoustic wave imaging apparatus.

Solution to Problem

This invention provides an acoustic wave imaging apparatus, comprising:

a plurality of acoustic wave receiving elements each receiving an acoustic wave emitted from an object, and converting the acoustic wave into a received signal;

a phase aligning unit which aligns phases of a plurality of received signals obtained from the plurality of acoustic wave receiving elements;

a complex signal acquiring unit which generates complex signals out of the phase-aligned received signals obtained by the phase aligning unit and acquires a plurality of complex signals;

a correlation matrix calculating unit which calculates a correlation matrix of the plurality of complex signals; and an electric power calculating unit which calculates constrained minimum power of the received signals, using the correlation matrix and a predetermined constraint vector, wherein the correlation matrix calculating unit calculates the correlation matrix at a predetermined cycle, and sequentially outputs the calculated correlation matrix to the electric power calculating unit, and the electric power calculating unit calculates a plurality of constrained minimum powers in parallel by use of the output correlation matrices, the plurality of constrained minimum powers are corresponding to the output correlation matrices respectively.

This invention also provides an acoustic wave imaging method, comprising:

a receiving step of receiving, by each of a plurality of acoustic wave receiving elements, an acoustic wave emitted from within an object and converting the acoustic wave into a plurality of receive signals;

a phase aligning step of aligning phases of the plurality of received signals obtained from the plurality of acoustic wave receiving elements;

a complex signal acquiring step of generating complex signals out of the phase-aligned received signals obtained in the phase aligning step and acquiring a plurality of complex signals;

a correlation matrix calculating step of calculating a correlation matrix of the plurality of complex signals; and an electric power calculating step of calculating constrained minimum power of the received signals, using the correlation matrix and a predetermined constraint vector, wherein in the correlation matrix calculating step the correlation matrix is calculated at a predetermined cycle and output sequentially, and in the electric power calculating step a plurality of constrained minimum powers are calculated in parallel by use of the output correlation matrices, the plurality of constrained minimum powers are corresponding to the output correlation matrices respectively.

Advantageous Effects of Invention

According to the present invention, calculation based on the CMP method can be processed at high-speed in the acoustic wave imaging apparatus.

Further features of the present invention will become apparent from the following description of exemplary embodiments with reference to the attached drawings.

DESCRIPTION OF EMBODIMENTS

Embodiments of the present invention will now be described with reference to the drawings.

Figure 1:
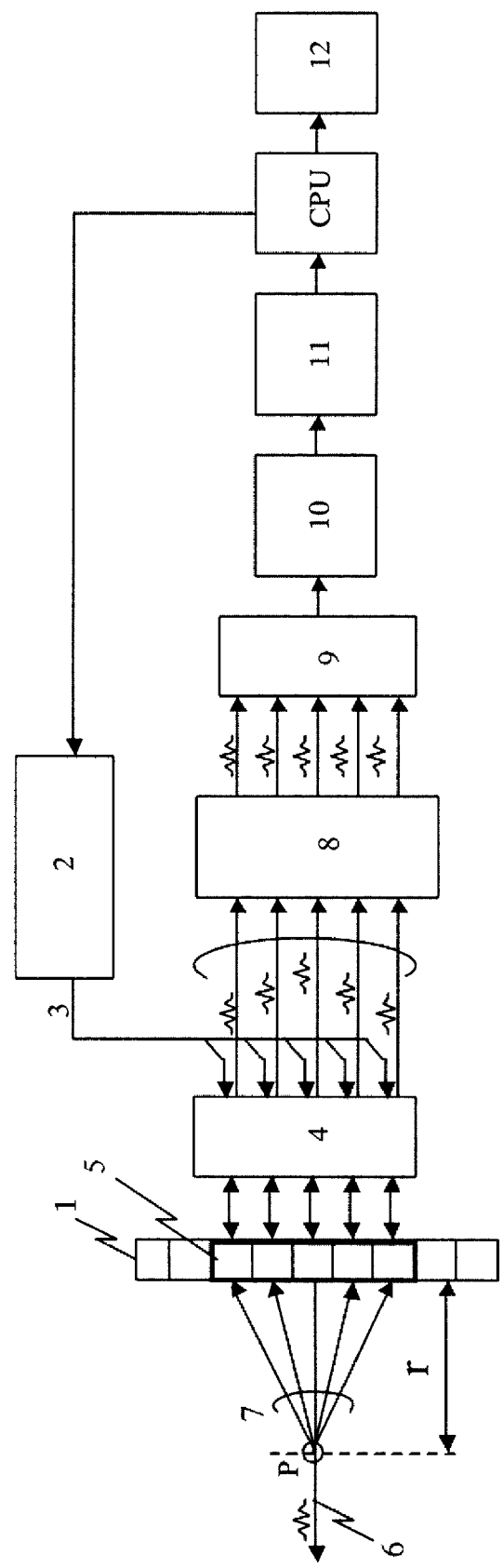
FIG. 1 is a diagram depicting a configuration of a conventional acoustic wave imaging apparatus.

FIG. 1 is a diagram depicting a configuration example of a conventional acoustic wave imaging apparatus. An ultrasound wave imaging apparatus which uses an ultrasound wave is shown here, but whether an acoustic wave is in the ultrasound wave region or not has no influence on the essence of the technology. In FIG. 1, a plurality of ultrasound wave transmitting/receiving elements are arrayed in an ultrasound probe 1. A transmission signal processing circuit 2 generates a transmission signal 3 based on an instruction from the CPU, which is an information processor, drives an ultrasound transmitting/receiving element group 5 via a switch circuit 4, and transmits a pulsed ultrasound beam 6.

Ultrasound echo waves 7 emitted by the reflection of the ultrasound beam 6 are converted into electric signals by the ultrasound wave transmitting/receiving element group 5, and these electric signals are sent to a phase aligning delay circuit 8 via the switch circuit 4. The phase aligning delay circuit 8 adjusts the delay time so that the arrival timings of echo signals from a given point P are aligned. The signals which were generated by the ultrasound echo waves from the same point P, and obtained and phase-aligned by the phase aligning delay circuit, become the power calculation targets in a one time processing. A totaling circuit 9 adds all the processing target signals whose arrival timings are aligned, and generates a strong received signal focused on the point P. The point P, from which the signals are received by the receiving elements, gradually becomes more distant on an ultrasound beam path as time elapses, and therefore if the delay time of the phase aligning delay circuit 8 is updated appropriately as time elapses, this strong echo received signal focusing in turn on all the points on the ultrasound beam path can be generated in real-time. In this case, interfering waves from locations other than the focus position are attenuated by this totaling since the respective delay time values are all different, and the signals generated by the ultrasound echo wave on the line of locations P making up the ultrasound beam path are obtained as a one-line received signal.

The one-line received signal which is output by the totaling circuit 9 is converted into an echo intensity waveform by an envelope detecting circuit 10, and then the information thereof is compressed by a LOG conversion circuit 11, and transferred to a CPU. The CPU collects the echo intensity waveform on each ultrasound beam path while appropriately instructing position and direction for transmitting the transmitted ultrasound beam, creates echo image data based on this echo intensity waveforms, and has a display apparatus 12 display the image.

Example 1

Figure 2:
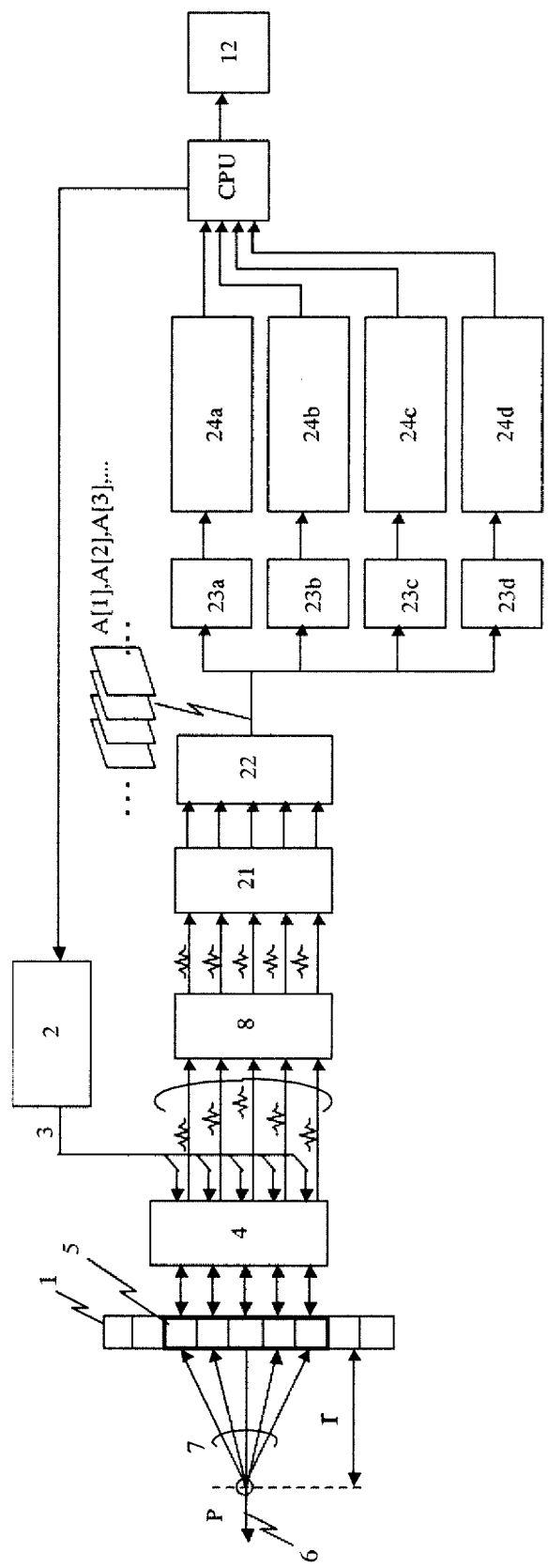
FIG. 2 is a diagram depicting a configuration of an acoustic wave imaging apparatus of the present invention.

FIG. 2 is a diagram depicting a configuration of an acoustic wave imaging apparatus of this example. This acoustic wave imaging apparatus, to which the CMP method is applied, is different from a conventional apparatus in the portion of received signal processing circuitry from the phase aligning delay circuit 8 to the CPU. This different circuit portion is a group of circuits for calculating the constrained minimum power value $P_{min}$ given by Expression (8) in real-time for the received signals whose arrival timings have been aligned by the phase aligning delay circuit 8 (that is, phase-aligned received signals).

A complex signal acquiring circuit 21 is a circuit for converting each received signal into a complex signal x[k, t]. In the processing to convert an input signal (the phase-aligned received signal) into a complex signal, the input signal is regarded as the real part, and a signal whose phase is shifted 90 degrees from that of the input signal is generated and regarded as the imaginary part. The 90 degree phase shifted signal can be generated by standard FIR filter processing, as mentioned later, and therefore the complex signal acquiring circuit can be implemented easily as a real-time circuit.

A complex correlation matrix calculating circuit 22 is a calculating circuit for calculating a correlation matrix A given by Expression (5) from the complex signal x[k, t], to acquire correlation matrix data. Each element of the correlation matrix can be calculated by products between each signal and cumulative addition within a predetermined time interval, as Expression (5) clearly shows. Therefore the real-time calculation can be easily implemented if a multiplication circuit and a cumulative addition circuit are combined for each element. As a result, the complex correlation matrix calculating circuit 22 can sequentially output one correlation matrix for each time interval Tm at which the cumulative processing is executed, as A[1], A[2], A[3] . . . .

The correlation matrix, which is sequentially output by the complex correlation matrix calculating circuit 22, is sequentially and cyclically stored in a plurality of storage circuits 23a, 23b, 23c and 23d. A plurality of constrained electric power calculating circuits 24a, 24b, 24c and 24d calculate the constrained minimum power values given by Expression (8) in parallel, using the stored correlation matrix and predetermined constraint vector C.

Figure 3:
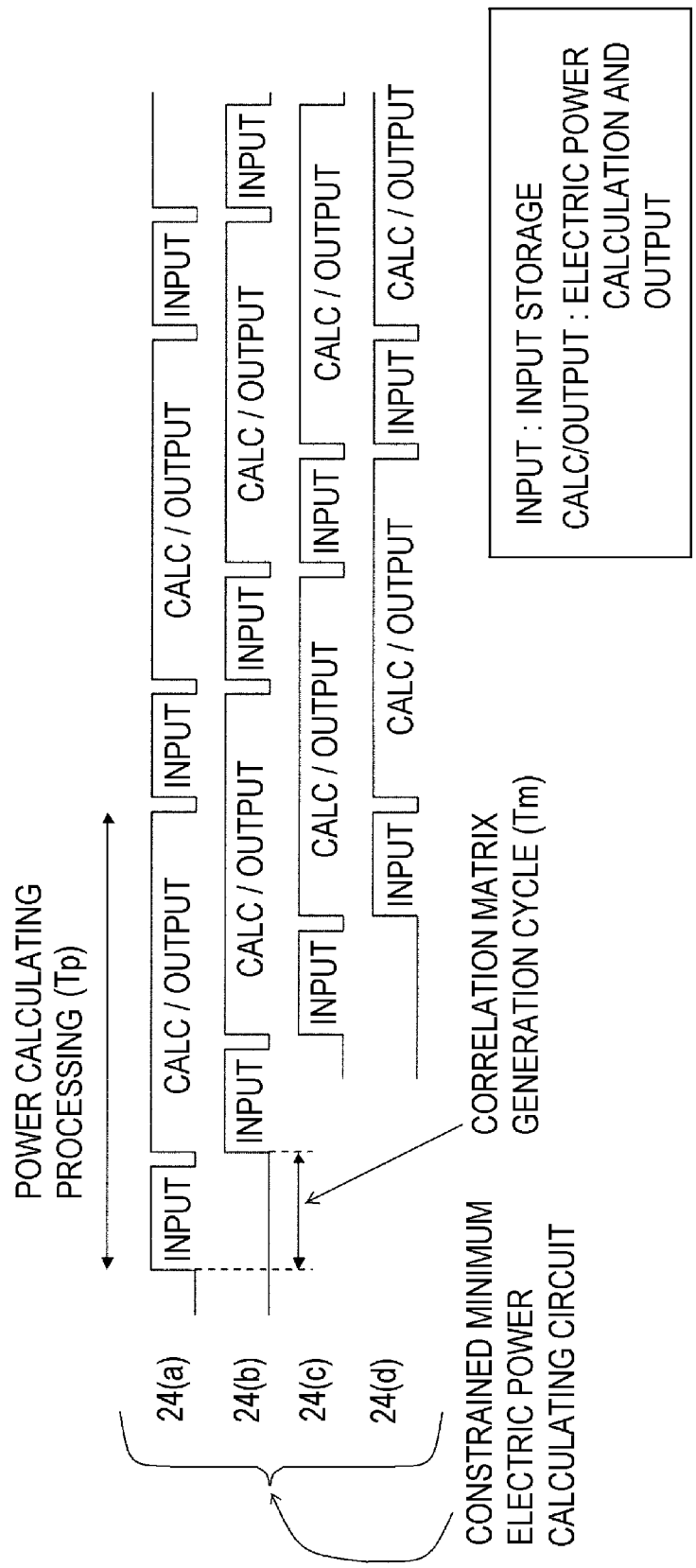
FIG. 3 is a time chart of a constrained power calculating circuit.

FIG. 3 is a concrete time chart of the operations of the constrained electric power calculating circuits 24a, 24b, 24c and 24d. As FIG. 3 shows, the four storage circuits 23a, 23b, 23c and 23d sequentially and cyclically input and store the correlation matrix data which is input from the correlation matrix calculating circuit in the previous stage at cycle Tm. While the next correlation matrix data is input to the same storage circuit, each constrained electric power calculating circuit 24a, 24b, 24c and 24d calculates the minimum electric power value, and outputs the result. Then even if the constrained electric power calculating circuit requires a processing time that is four times that of the correlation matrix generation time Tm, the entire processing, from signal input to electric power calculation (electric power calculating processing Tp), can be executed in real-time. The required number of processings N that is/are executed in parallel by the constrained minimum power calculating circuit 24 must satisfy N>=Tp/Tm.

The phase aligning delay circuit corresponds to what is sometimes termed herein the "phase aligning unit" of the present invention. The complex signal acquiring circuit corresponds to the complex signal acquiring unit of the present invention. The complex correlation matrix calculating circuit corresponds to the complex correlation matrix calculating unit. The constrained electric power calculating circuit corresponds to the electric power calculating unit of the present invention. The CPU, which is an information processing unit, creates image data based on calculated electric power, in other words, the CPU plays a function of image creating unit of the present invention.

Generally speaking, the constrained minimum power calculation is processing which takes time due to such processing as inverse matrix processing, but it is obvious that the entire processing, from the signal input to electric power calculation, can be executed in real-time if a required number of circuits are provided for parallel calculation. If a minimum electric power value calculated in real-time like this is transferred to the CPU, and the CPU reconstructs an echo image and displays it on the display apparatus 12, then an acoustic wave imaging apparatus based on the CMP method can be implemented at a commercially feasible processing speed.

A concrete example of each processing block will now be described, so as to show that each processing block can be implemented at a commercially feasible scale.

Figure 4:
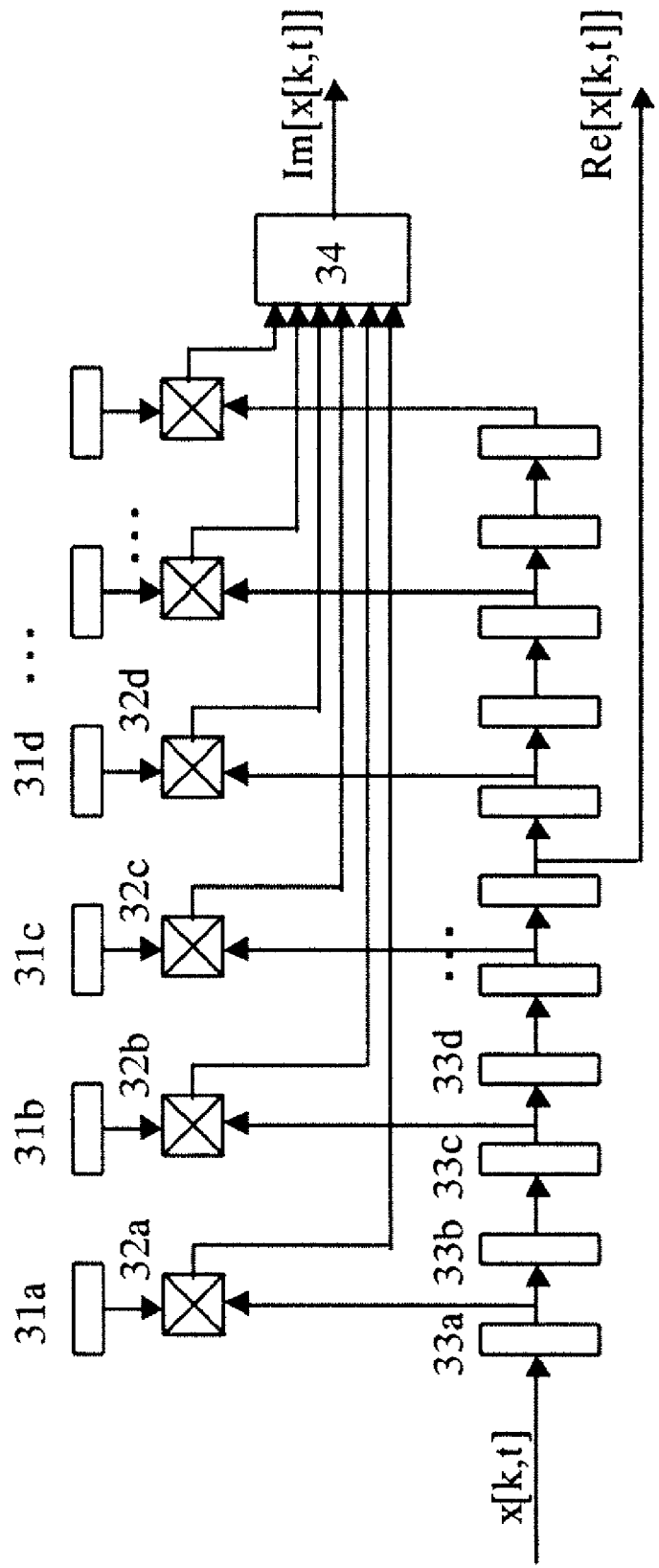
FIG. 4 is a diagram depicting a configuration of a complex signal acquiring circuit.

FIG. 4 is a diagram depicting a concrete configuration of the complex signal acquiring circuit 21. In a processing for complexifying a digital input signal constituted by a series of real values, the input signal is regarded as the real part, and a signal whose phase is shifted 90 degree from that of the input signal is calculated and regarded as the imaginary part, as mentioned above. The processing for generating a signal with the phase shifted 90 degree from the input signal can be easily implemented by an FIR (Filter Impulse Response) filter, which has an odd number of taps and odd symmetry coefficients according to filter theory. A band pass filter, which is an FIR filter having an odd number of taps and odd symmetry coefficients and whose gain characteristic is "1" in a predetermined frequency region, can be implemented by a filter of which the even number coefficient is "0".

In FIG. 4, 33a, 33b, 33c, . . . are shift registers (labeled "SR") which shift and hold the digital signals x[k, t]; (t=0, 1, 2, . . . ) being input according to a reference clock. 31a, 31b, 31c, . . . are registers (labeled "R") for storing coefficients of the FIR filter, elements 32a, 32b, 32c, . . . are multiplication circuits which multiply a coefficient and input signal, and 34 is an addition circuit. As mentioned above, among the coefficients of the FIR filter to be implemented, the coefficient in an even number place from the center is "0", so the imaginary part Im[x[k,t]] of the output signal can be calculated by multiplying each input signal and coefficient and adding the results, excluding the coefficient "0" portions. For the output Re[x[k, t]] of the real part, an input signal is delayed for the amount of delay required for the calculation of the imaginary part due to the filter, and outputs the result. In this way the input signal x[k, t], which is input as a series of real numbers, can be converted into a new complex signal x[k, t], and output.

Figure 5:
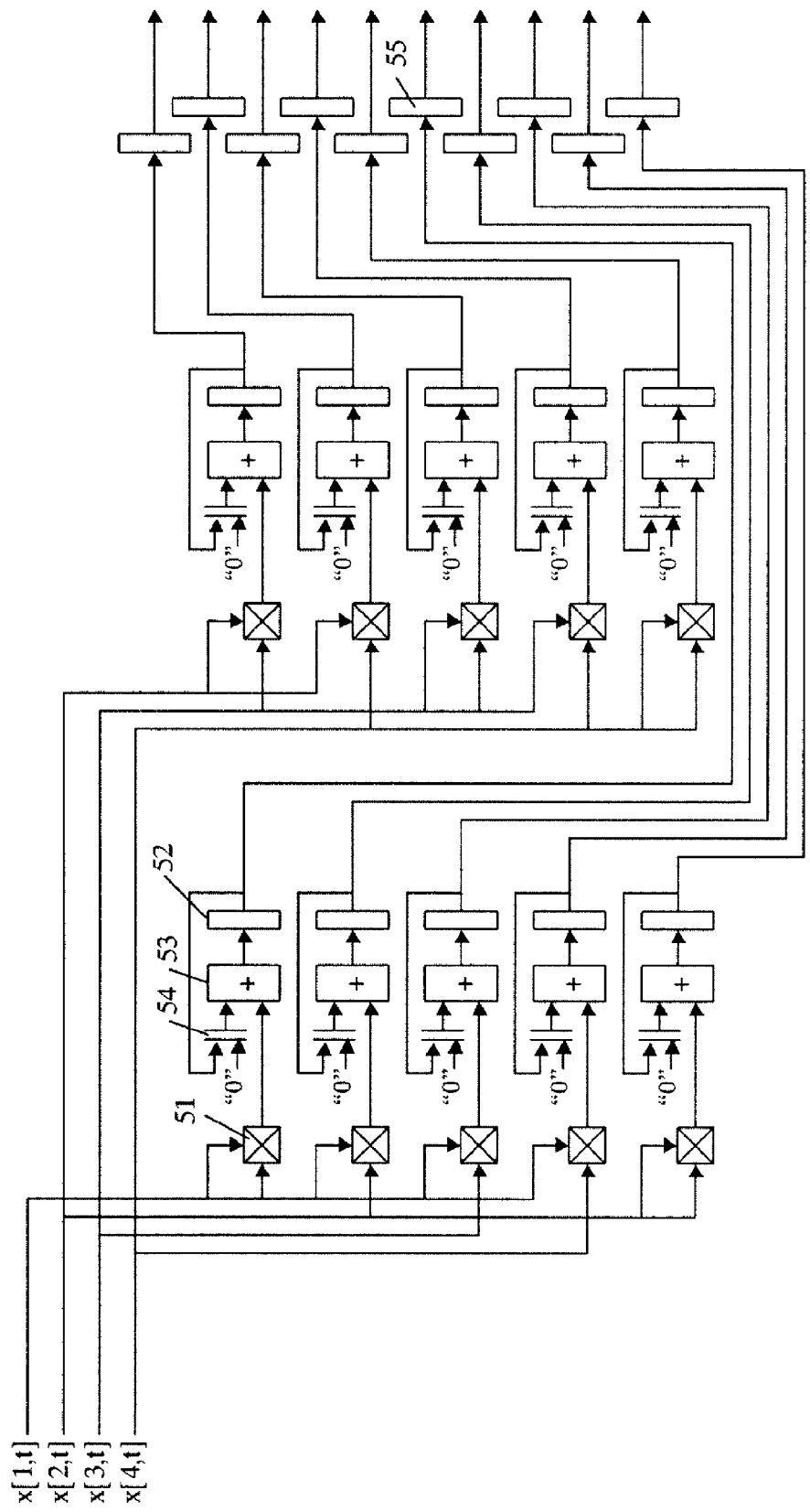
FIG. 5 is a diagram depicting a configuration of a complex correlation matrix calculating circuit.

FIG. 5 is a diagram depicting a concrete configuration of the complex correlation matrix calculating circuit 22. In FIG. 5, x[1, t], x[2, t], x[3, t] and x[4, t] are four received signals converted into complex signals, and in FIG. 5, only the upper triangular elements of the 4*4 matrix are calculated. As the calculation of Expression (5) shows, j*i elements and i*j elements are in a complex conjugate relationship in the correlation matrix, therefore it is sufficient if only ten upper triangular elements, including diagonal elements, are calculated.

To calculate each element of the correlation matrix, each signal to be input as shown in FIG. 5 is multiplied in each combination, and the result is cumulatively added within a predetermined time range. For example, the multiplier 51 multiplies an input x[1, t] by a complex conjugate of x[1, t], and the result is cumulatively added by an adder 53 and a cumulative register 52.

In other words, in the beginning of the cumulative addition, a selection circuit 54 selects a "0" signal, and directly sets the output of a multiplication circuit 51 in the cumulative register 52. While the cumulative addition continues, the selection circuit 54 selects the current content of the cumulative register 52, and so adds the output of the multiplication circuit 51 to the current content of the cumulative register 52, and sets the result in the cumulative register 52 again. The cumulatively calculated result is transferred to an output register 55 in the beginning of the next cumulative addition. For the other elements of the correlation matrix as well, similar processing is performed whereby each element of the correlation matrix is calculated and output in a predetermined cycle. The number of multipliers required increases in proportion to the square of the number of input signals, but even an FPGA (Field Programmable Gate Array), which is a simplified LSI (Large Scale Integration), encloses 1000 or more multipliers, so one FPGA is sufficient to implement this calculation by means of ordinary technical ideas such as increasing the speed of the calculation clock.

Figure 6A:
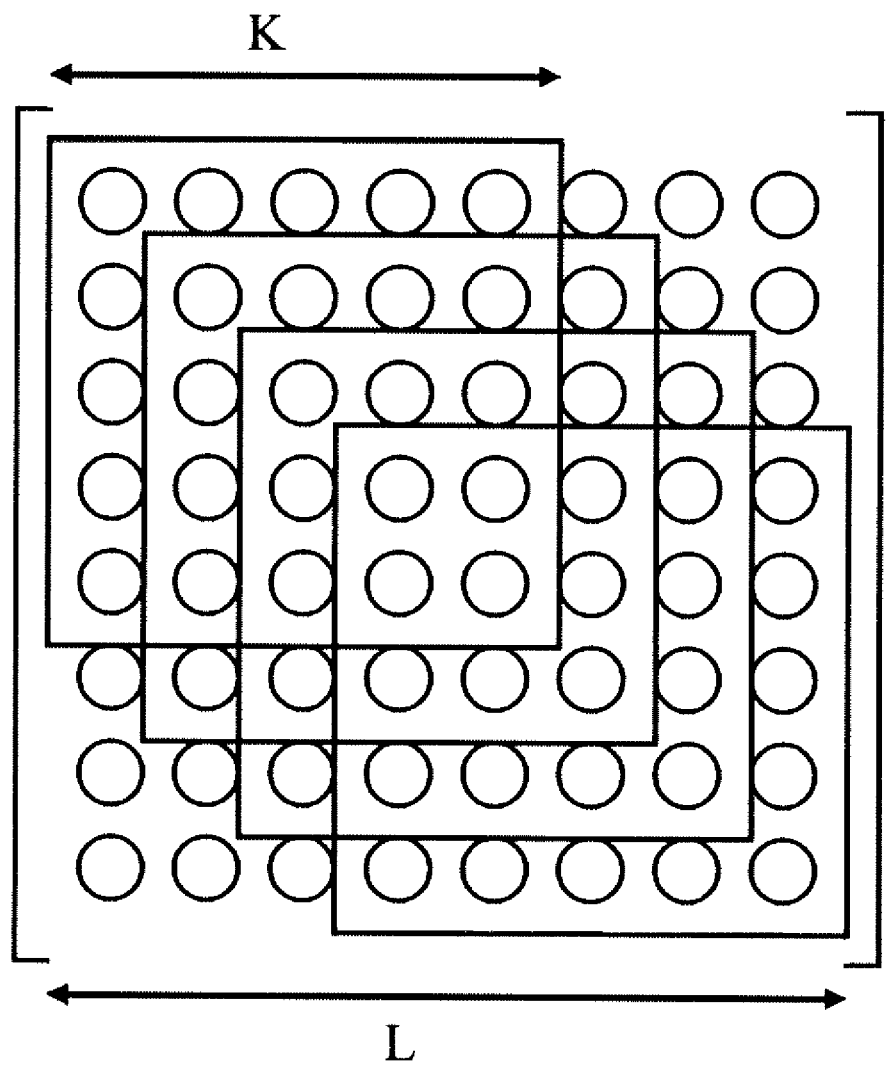
FIG. 6A is a diagram depicting a spatial averaging processing.

The calculated correlation matrix can be directly used for calculating the constrained minimum power, but in order to stabilize the calculation result, it is preferable to perform spatial averaging processing, as shown in FIG. 6, on a calculated correlation matrix, so as to convert to a reduced correlation matrix. FIG. 6A is a diagram depicting a spatial averaging processing for creating a corrected 5*5 correlation matrix from an 8*8 correlation matrix. The spatial averaging processing is a processing that involves extracting a K*K partial matrix from an L*L matrix in a diagonal direction, as shown in FIG. 6A, and adding the extracted matrices to calculate a K*K correlation matrix.

Figure 6B:
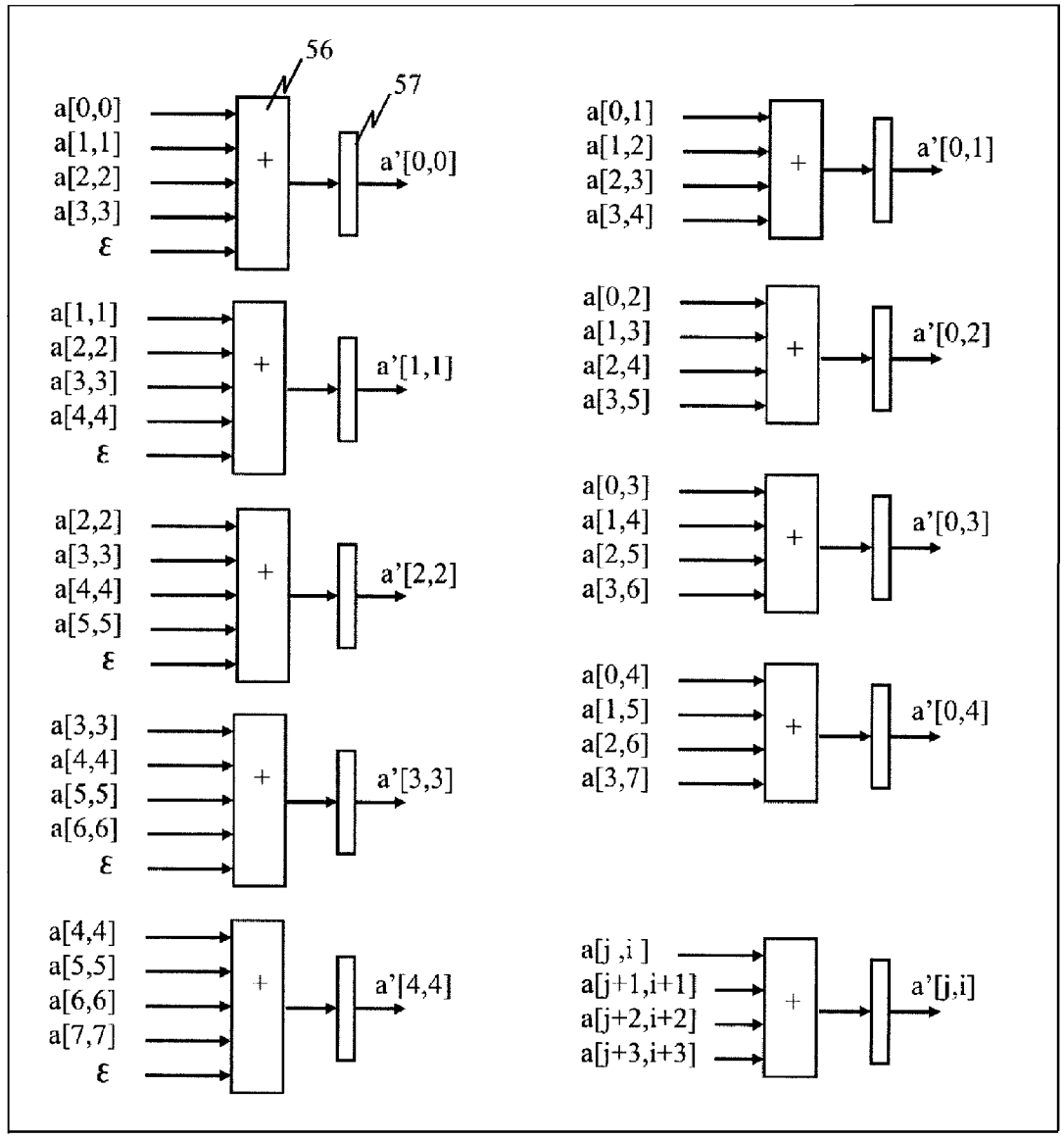
FIG. 6B is a diagram depicting a spatial averaging processing.

FIG. 6B is a diagram depicting a concrete configuration of a circuit for performing the spatial averaging processing in real-time. Each element a[0, 0], a[0, 1], . . . of a correlation matrix A to be input is output in parallel from the complex correlation matrix calculating circuit 22 in FIG. 5. Therefore the spatial averaging processing requires only selecting the necessary matrix elements a[0, 0], a[1, 1], a[2, 2] and a[3, 3], adding these elements by means of the addition circuit 56, and setting the addition result in the output register 57 as the upper left circuit portion of FIG. 6B shows. In FIG. 6B, the circuit group on the left side is a group of examples of circuits for calculating diagonal elements. For a diagonal element, an infinitesimal positive number epsilon is also added to stabilize the inverse matrix calculation by guaranteeing the existence of an inverse matrix. The right side of FIG. 6B shows calculation circuit examples for elements excluding the diagonal elements. If the spatial averaging processing was performed, the result of the spatial averaging processing becomes a new complex correlation matrix, and is used for the subsequent processing.

Figure 6C:
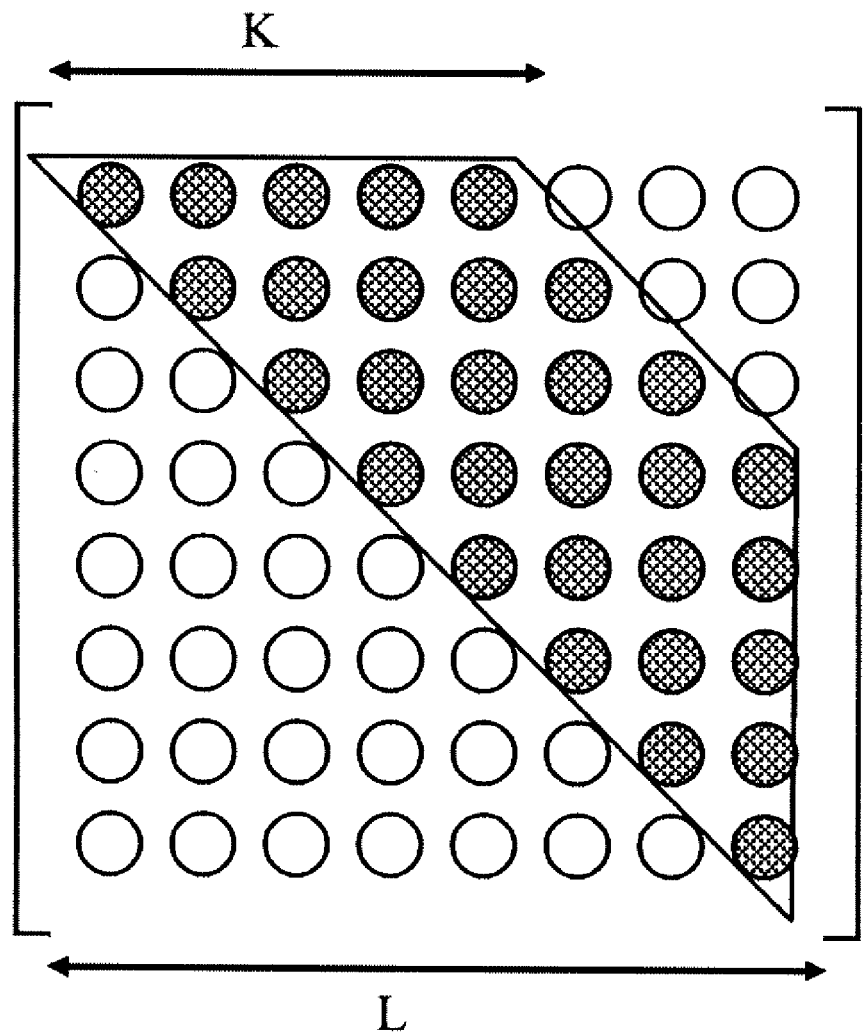
FIG. 6C is a diagram depicting a spatial averaging processing.

FIG. 6C shows the elements of the input matrix required for the spatial averaging processing. It is sufficient that the input correlation matrix has the elements of the upper triangular portion, as mentioned above, but the calculation of elements which are not used for the spatial averaging processing can also be omitted. In this case, the matrix elements to be calculated in the complex correlation matrix in the previous stage are only those in the shaded portion in FIG. 6C, and the circuit scale can thus be further reduced by the spatial averaging processing.

Figure 7:
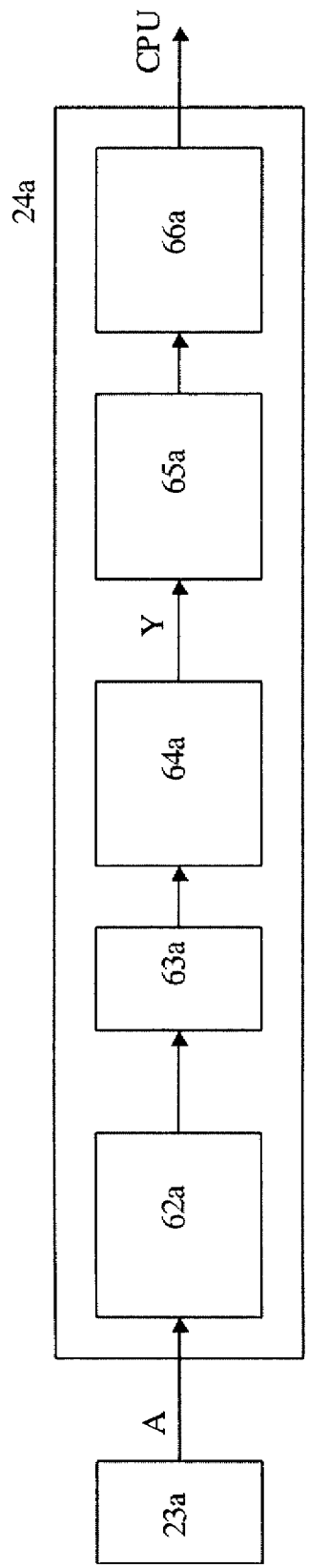
FIG. 7 is a diagram depicting a configuration of a constrained power calculating circuit.

FIG. 7 is a diagram depicting a concrete configuration of the constrained electric power calculation circuit. The calculation of the constrained minimum power is a processing for calculating the minimum receiving electric power $P_{min}$ given by Expression (8) using a correlation matrix A calculated in the previous stage and a predetermined constraint vector C.

The calculation of Expression (8) can be divided into a step given by Expression (9) and a step given by Expression (10) because of the form of the expression.

Expression (9) shows a step of calculating the solution Y of the simultaneous linear equations:

[Math. 9]

$$AY = C \qquad (9)$$

Expression (10) shows a step of calculating a reciprocal number of the inner product of Y and the constraint vector C:

[Math. 10]

$$P_{min} = \frac{1}{C^H Y} \qquad (10)$$

The calculation processing for determining the solution Y of the simultaneous linear equations (9) can be further divided into a QR decomposition processing for converting the coefficient matrix A into an upper triangular matrix, and a backward substitution processing for solving the simultaneous linear equations the coefficients of which are an upper triangular matrix.

In the QR decomposition processing, Expression (11), which is a set of simultaneous linear equations denoted by developing Expression (9) into elements, is used:

[Math. 11]

$$\begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix} \begin{bmatrix} y_1 \\ y_2 \\ y_3 \\ y_4 \end{bmatrix} = \begin{bmatrix} c_1 \\ c_2 \\ c_3 \\ c_4 \end{bmatrix} \qquad (11)$$

Then Expression (11) is multiplied by an appropriate rotational matrix from the left side, so as to be converted into simultaneous linear equations whose coefficients are the upper triangular matrix given by Expression (12):

[Math. 12]

$$\begin{bmatrix} r_{11} & r_{12} & r_{13} & r_{14} \\ 0 & r_{22} & r_{23} & r_{24} \\ 0 & 0 & r_{33} & r_{34} \\ 0 & 0 & 0 & r_{44} \end{bmatrix} \begin{bmatrix} y_1 \\ y_2 \\ y_3 \\ y_4 \end{bmatrix} = \begin{bmatrix} b_1 \\ b_2 \\ b_3 \\ b_4 \end{bmatrix} \qquad (12)$$

The backward substitution processing is a processing for calculating the Y vector, which is the solution of Expression (12), according to the backward substitution procedure given by Expression (13):

[Math. 13]

$$y_4 = \frac{1}{r_{44}} \cdot b_4$$

$$y_3 = \frac{1}{r_{33}} \cdot (b_3 - r_{34} \cdot y_4)$$

$$y_2 = \frac{1}{r_{22}} \cdot (b_2 - r_{24} \cdot y_4 - r_{23} \cdot y_3)$$

$$y_1 = \frac{1}{r_{11}} \cdot (b_1 - r_{14} \cdot y_4 - r_{13} \cdot y_3 - r_{12} \cdot y_2)$$

(13)

FIG. 7 is a diagram depicting a concrete configuration of one constrained electric power calculating circuit 24a separated according to the above mentioned steps. In other words, a QR decomposition calculating circuit 62a inputs the correlation matrix A stored in the storage circuit 23a in the previous stage as the coefficient matrix of Expression (11), calculates the elements of the upper triangular matrix and constant terms given by Expression (12), and outputs the result to a coefficient storage circuit 63a. Based on the elements and constant terms of the upper triangular matrix stored in the coefficient storage circuit 63a, a backward substitution calculating circuit 64a determines a solution vector Y of the simultaneous linear equations (11) according to the calculation procedure of Expression (13), and outputs the result.

A product sum calculating circuit 65a is a circuit for calculating a denomination of the right hand side of Expression (10) as an inner product of the constraint vector C and the solution vector Y, and outputs a reciprocal number of the constrained minimum power $P_{min}$, which is a result of the inner product. The calculated reciprocal number of $P_{min}$ may be directly transferred to the CPU. In many cases the density values of an echo image are used by performing LOG (logarithmic) conversion on an electric power value, therefore, according to the present embodiment, a LOG conversion circuit 66a in the subsequent stage performs LOG conversion on the reciprocal number of the calculated power value, and transfers the result to the CPU accordingly. The LOG converted value of the reciprocal number is mathematically the same as the converted value, but with the sign inverted, and hence this procedure does produce any problems.

For a concrete calculation procedure for the QR decomposition, many numerical value calculation algorithms, including a Gaussian elimination method and Givens Rotation, are known, and it is technically possible to implement this calculation procedure using digital circuits. For the backward substitution processing as well, digital circuits can be designed according to the calculation procedure of Expression (13). Therefore the constrained minimum power calculation can be implemented by digital circuits.

Figure 8:
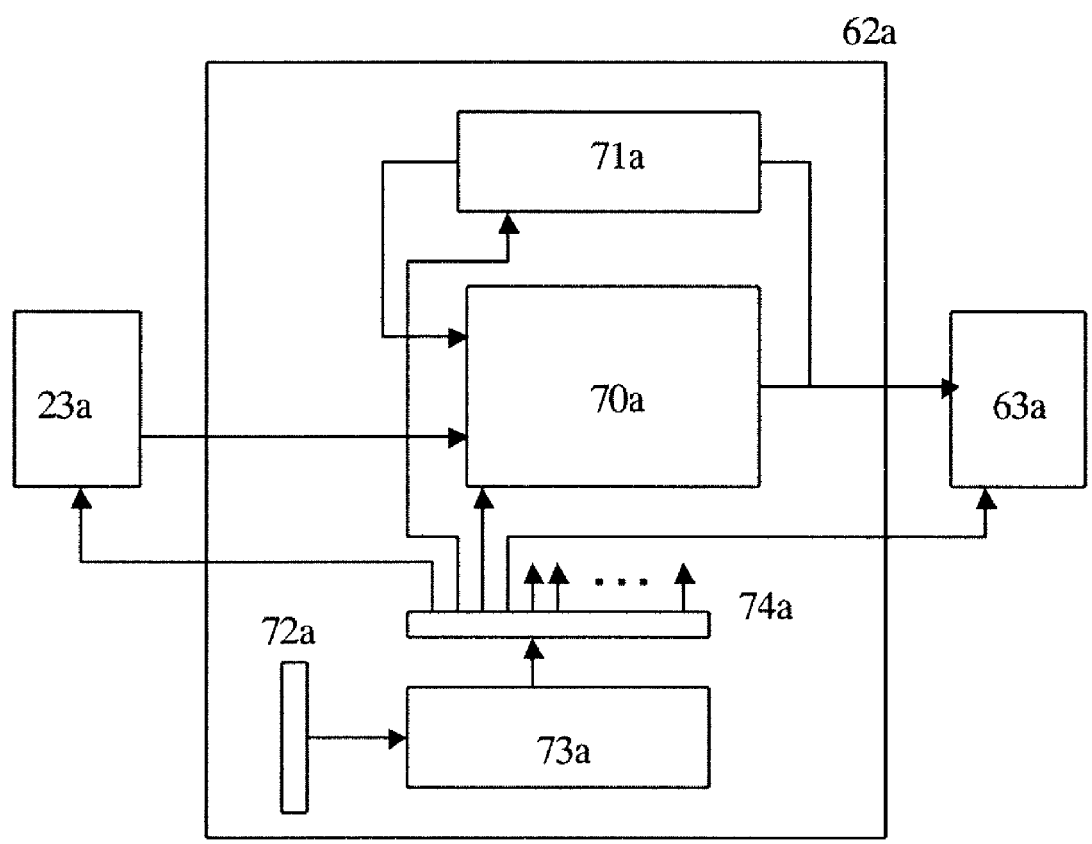
FIG. 8 is a diagram depicting a configuration of a QR decomposition circuit.

FIG. 8 is a diagram depicting a concrete configuration for implementing the QR decomposition circuit 62a as a relatively compact circuit. For the QR decomposition processing, a procedure to erase "0" in one of the lower left matrix elements is repeated so as to clear "0" in all the lower left elements in the above mentioned Gaussian elimination method or Givens Rotation. Hence a calculation procedure to clear "0" in one element, or one calculation procedure when the above calculation procedure is decomposed into smaller basic calculation steps, is implemented as a QR decomposition basic calculating circuit, and is repeatedly executed in a micro-program format while switching the input data. Thereby the QR decomposition calculation circuit can be implemented as relatively compact circuit.

The QR decomposition circuit 62a in FIG. 8 is an embodiment based on this concept. In FIG. 8, a QR decomposition basic calculating circuit 70a executes basic computation. The QR decomposition basic calculating circuit 70a repeats inputting the elements of the correlation matrix A stored in the input storage circuit 23a and an intermediate result stored in an intermediate storage circuit 71a, and outputting the calculation result back to the intermediate storage circuit 71a or the coefficient storage circuit 63a. The lower portion in FIG. 8 is a micro-program portion for controlling this calculation procedure. Each time a micro-program counter 72a is incremented, a micro-program code, the address of which is a value of the micro-program counter 72a, is read from a micro-program memory 73a to a command register 74a. Based on the content of the command register 74a, an operation timing and an address of each storage circuit and the calculation function of the QR decomposition basic calculating circuit 70a are controlled.

In the circuit having this configuration, the QR decomposition calculating processing can be executed at a predetermined interval, if the micro-program counter 72a is started from the initial value every time a new correlation matrix data is input from the previous stage.

Figure 9:
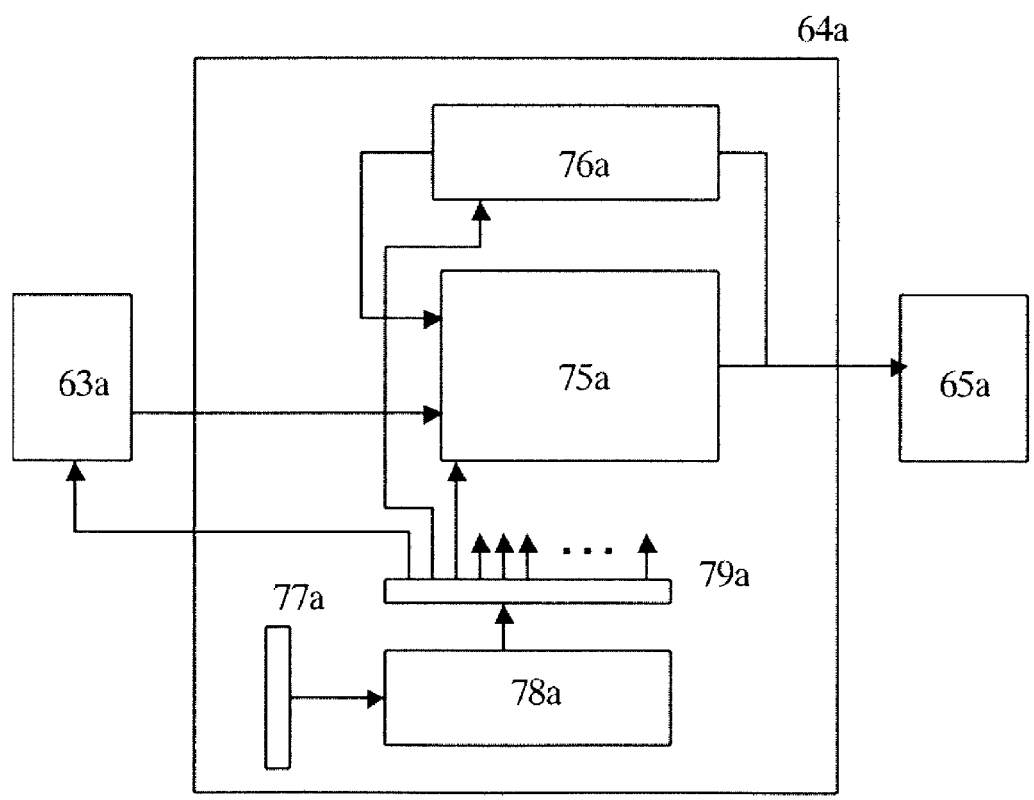
FIG. 9 is a diagram depicting a configuration of a backward substitution calculating circuit.

FIG. 9 is a diagram depicting another concrete configuration of the backward substitution calculating circuit 64a. The backward substitution calculating circuit 64a can be implemented using exactly the same control circuit method as the QR decomposition calculating circuit 62a by extracting the basic calculation functions of Expression (13) and implementing these functions as a backward substitution basic calculating circuit 75a. By constructing the QR decomposition calculating circuit and the backward substitution calculating circuits, which require large-volume calculation, as the calculating circuits controlled by a micro-program like this, the circuit scale of the entire apparatus can be reduced to a commercially feasible scale.

Example 2

Figure 10:
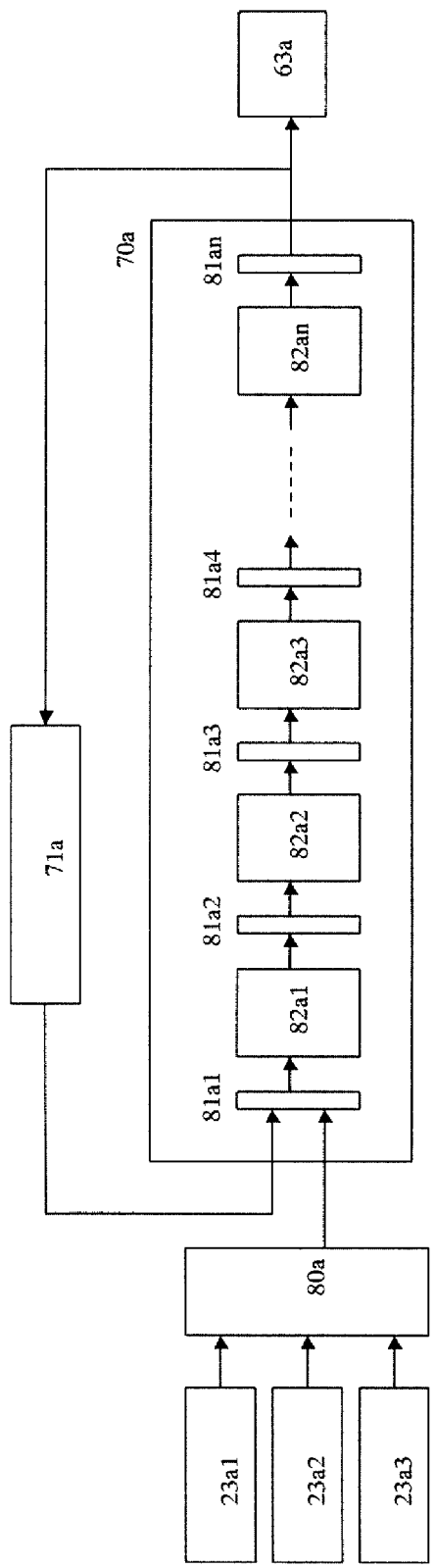
FIG. 10 is a diagram depicting a configuration of a QR decomposition basic calculating circuit of Example 2.

In this example, a case of constructing the QR decomposition basic calculating circuit 70a in FIG. 8 as a pipeline type calculating circuit, which is suitable for high-speed calculation, will be described. FIG. 10 is a diagram depicting this QR decomposition basic calculating circuit 70a. A pipeline type circuit is comprised of registers 81a1, 81a2, 81a3, ..., 81an array tandem, and calculation circuits 82a1, 82a2, 82a3, ..., 82an. The data being set in the input register 81a is sequentially shifted to the subsequent registers 81a2, 81a3, ... according to the basic clock. Calculation processing is performed on the shifted data gradually by the calculating circuits 82a1, 82a2, 82a3, ..., 82an at every time shift, and the input data is converted into the final result when processing reaches the register 81an in the final stage.

If a circuit having this configuration is used, different input data can be set at each clock, and hence a complicated calculation processing can be executed at high-speed of 1 calculation/clock, although it takes time to reach the final result.

In order to design the QR decomposition circuit according to a Givens Rotation algorithm, many vector rotation calculations must be processed at high-speed. The vector rotation calculation is normally a complicated calculation involving square roots and multiplication. Therefore if an algorithm known as a CORDIC algorithm is used, this vector rotation calculation can be executed by repeating simple integer type calculations comprised of shift operations and additions/subtractions, and can be easily implemented using the above mentioned pipeline type circuit. As a consequence, if the CORDIC algorithm implemented by the pipeline type circuit is used as the basic circuit of the QR decomposition processing, both an increase in speed and decrease in size of the circuit can be easily achieved.

In the case of the pipeline type circuit however, it takes n clocks to obtain a calculation result of one body of input data. Therefore, in the case of the QR decomposition processing and the backward substitution processing in which a calculation result is used for the calculation in the next step, the input of the next calculation data delays, and calculation efficiency drops. In order to avoid this problem, calculations for a plurality of correlation matrices A[1], A[2] and A[3] are executed in parallel in one pipeline type processing circuit 70a in the example in FIG. 10.

In other words, when the correlation matrices A[1], A[2] and A[3] are calculated, calculation data which is ready is set with priority in the input register 81a1 of the pipeline calculating circuit, and so the operating ratio of the pipeline calculating circuit can be improved. If the number of correlation matrices to be calculated in parallel is appropriately selected, the pipeline calculating circuit can be constructed to execute the basic calculation in about 1 clock time on average, and hence a circuit of both even smaller size and faster speed can be implemented using this circuit type.

For example, the number of times of vector rotation calculations required for the QR decomposition is approximately 90 when the size of the correlation matrix A is 6*6. As mentioned above, if the vector rotation calculation is implemented using a pipeline type circuit based on the CORDIC algorithm, the net calculation time is 90 clocks. However, queuing occurs because one calculation result is used for the next calculation, and the actual calculation time dramatically increases, to about 800 clocks. In this case, the operating ratio of the pipeline circuit is approximately 11%, which is very low. If eight correlation matrices are calculated in parallel, the operating ratio of the pipeline circuit improves to about 86%, and the processing time required for the QR decomposition of eight correlation matrices can be within about 960 clocks.

The basic circuit of the CORDIC algorithm, which is a simple circuit comprised of a shift and integer type addition/subtraction, can be driven with 200 MHz or higher basic clocks, even if an FPGA, which is a simplified LSI, is used. In the case of driving the basic circuit at 200 MHz, in order to implement a 5 MHz or faster calculation cycle which is required for acoustic wave echo image processing, it is sufficient if the calculation time for one correlation matrix is kept to within 40 clocks. According to the above mentioned circuit configuration, the QR decomposition time required for one correlation matrix is 120 clocks, hence if the above mentioned three circuits are disposed and driven in parallel, the QR decomposition time for one correlation matrix can be 40 clocks, and a 5 MHz or higher calculation cycle can be implemented.

If the size of the correlation matrix A is 8*8, a required calculation volume is about double that of the case of a 6*6 matrix, then a 5 MHz or higher calculation cycle can be implemented if six of the above mentioned circuits are disposed. This level of circuit scale can be easily packaged in one FPGA, and an even smaller size and faster speed of the circuit can be implemented, as mentioned above.

This circuit system can also be applied to a backward substitution basic calculating circuit in the same way. In other words, the backward substitution basic calculating circuit is implemented as a pipeline type circuit system, and the backward substitution processing is executed for a plurality of matrices in parallel, then both smaller size and faster speed can be implemented in the backward substitution calculating circuit as well. As described above, if at least one of the QR decomposition processing and the backward substitution processing is calculated by the pipeline system, the processing speed can be faster.

Figure 11:
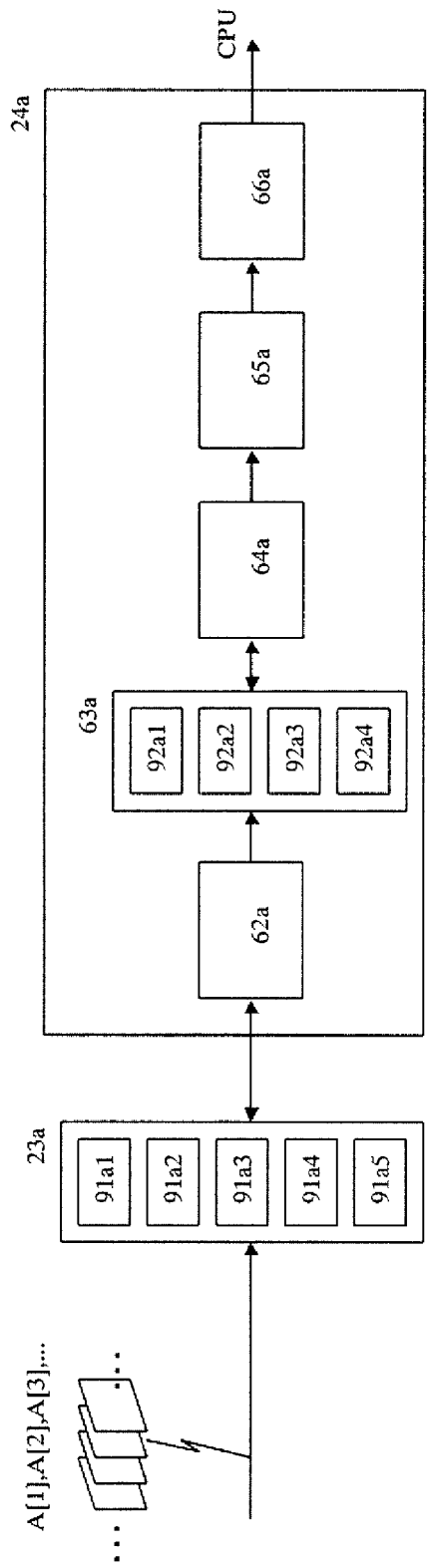
FIG. 11 is a diagram depicting a configuration of a constrained power calculating circuit of Example 2.

FIG. 11 is a diagram depicting another configuration of the storage circuit 23a and the constrained electric power calculating circuit 24a based on the above mentioned concept. In the storage circuit 23a, a plurality of correlation matrices 91a1, 91a2, . . . are stored, and calculations on the stored plurality of correlation matrices are executed in parallel in one QR decomposition calculating circuit 62a. The calculated results are stored in the coefficient storage circuit 63a as coefficient matrices 92a1, 92a2, . . . , and the backward substitution calculating circuit 64a executes the backward substitution calculation on the plurality of coefficient matrices 92a1, 92a2, . . . in parallel.

Figure 12:
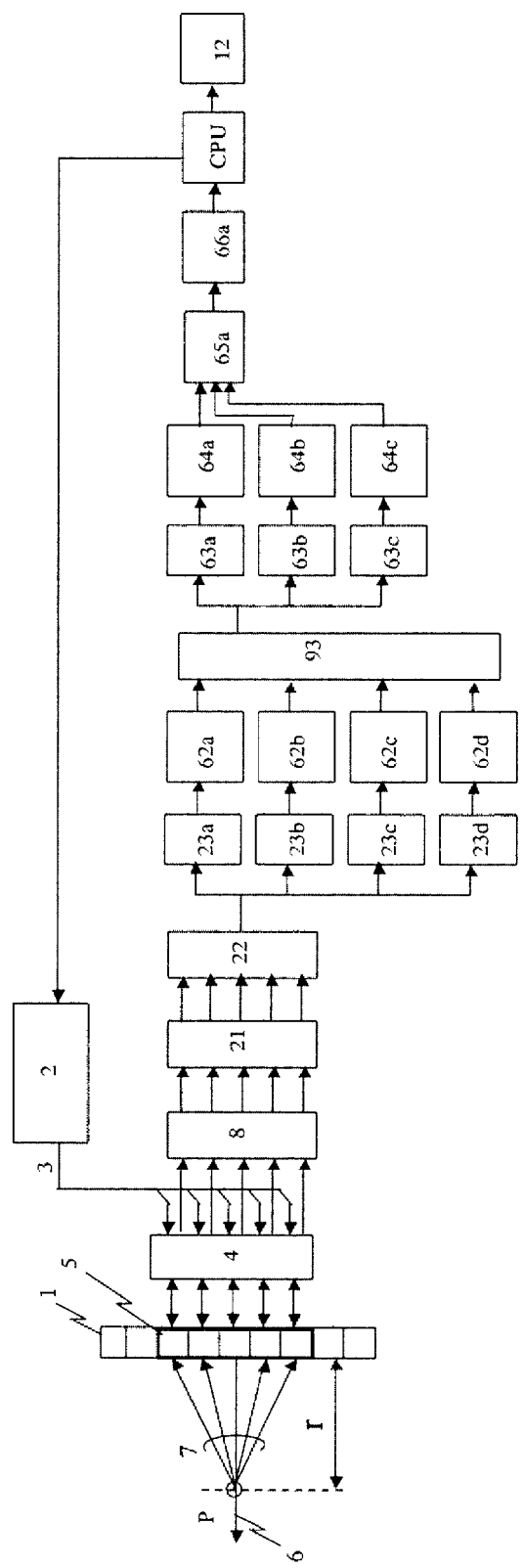
FIG. 12 is a diagram depicting a configuration of an acoustic wave imaging apparatus of Example 2.

FIG. 12 is a diagram depicting a configuration of an acoustic wave imaging apparatus using the storage circuit and the constrained electric power calculating circuit shown in FIG. 11. In FIG. 12, 23a, 23b, . . . are the storage circuits which store a plurality of correlation matrices respectively. 62a, 62b, . . . are the QR decomposition circuits which perform QR decomposition in parallel on the plurality of correlation matrices stored in the storage circuits 23a, 23b, . . . respectively. 93 is a distribution circuit which distributes and stores the coefficient matrices, which are sequentially output from each QR decomposition circuit, into the coefficient storage circuits 63a, 63b, . . . 64a, 64b . . . are the backward substitution calculating circuits which execute the backward substitution calculation in parallel on a plurality of coefficient matrices stored in the coefficient storage circuits 63a, 63b, . . . respectively. 65a is a product sum calculating circuit which calculates an inner product of a solution vector Y of simultaneous linear equations, which are sequentially output from the backward substitution calculating circuits and a predetermined constraint vector. 66a is a LOG conversion circuit which performs LOG conversion on the output of the product sum calculation circuit, transferring the result to the CPU.

By using the above mentioned configuration, the constrained electric power calculating circuit can select an optimum number of calculations to be executed in parallel for each calculation step. Critical here is that a plurality of matrices are calculated in parallel so that an effective constrained electric power calculation time for one matrix becomes a correlation matrix generation cycle or less, whereby an echo image signal based on the CMP method is generated almost at the same time as acoustic wave echo signal reception. As long as this condition is satisfied, various circuit configurations are possible. By each calculation circuit having such a configuration, the apparatus can be implemented with a commercially feasible circuit scale.

Example 3

Figure 13A:
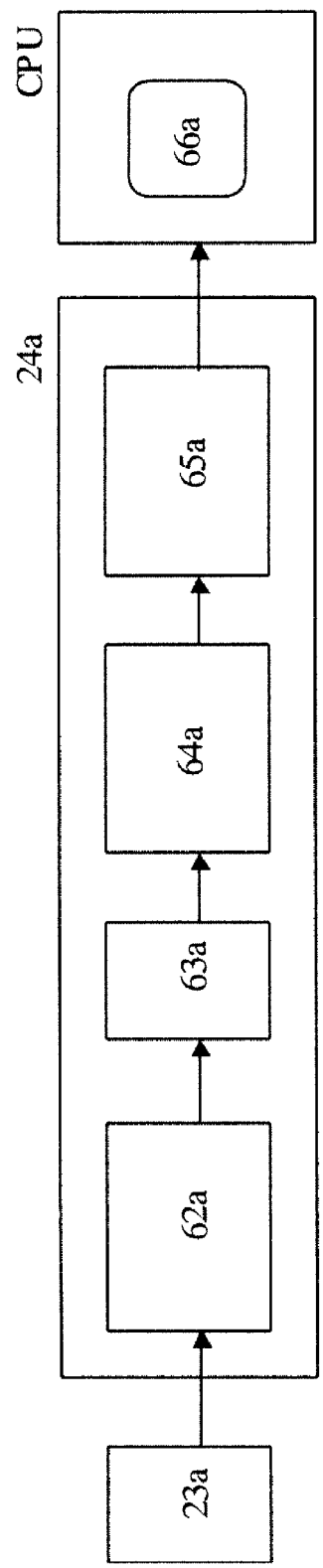
FIG. 13A is a diagram depicting a configuration of a constrained power calculating circuit of Example 3.
Figure 13B:
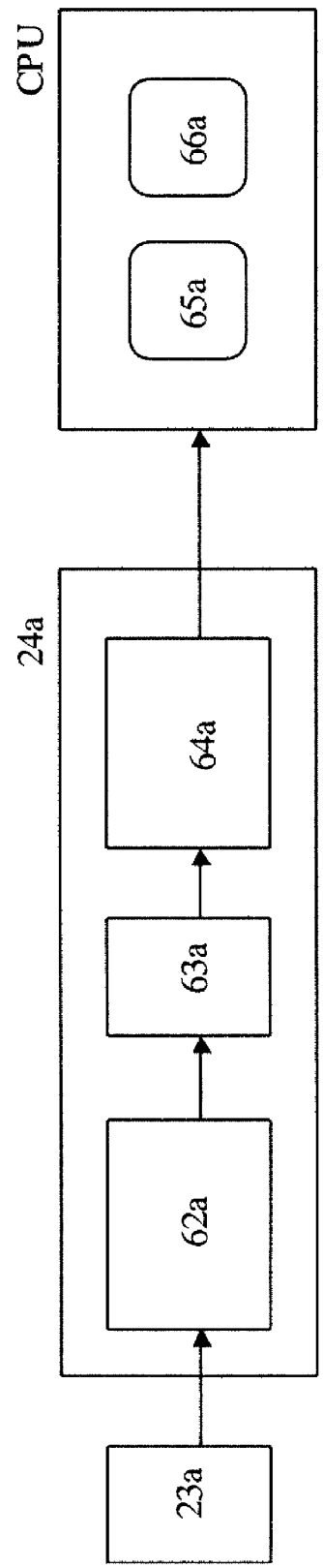
FIG. 13B is a diagram depicting a configuration of a constrained power calculating circuit of Example 3.

In the present example, an acoustic wave imaging apparatus, of which constrained electric power calculating circuit has a different configuration from those of the above examples, will be described. FIGS. 13A and 13B are diagrams depicting configurations of the constrained electric power calculating circuit of this example. The constrained minimum power calculation can be separated into and constituted by the QR decomposition, backward substitution, product sum calculation and LOG conversion, as mentioned above. Among these circuits, separated like this, QR decomposition requires the highest calculation volume, the backward substitution calculation circuit requires the second highest calculation volume, and the product sum calculation and LOG conversion circuits require relatively low calculation volumes. Therefore, in order to decrease the overall amount of circuitry, the CPU shares the calculation in the post-stages where the calculation volume is low.

Figure 13C:
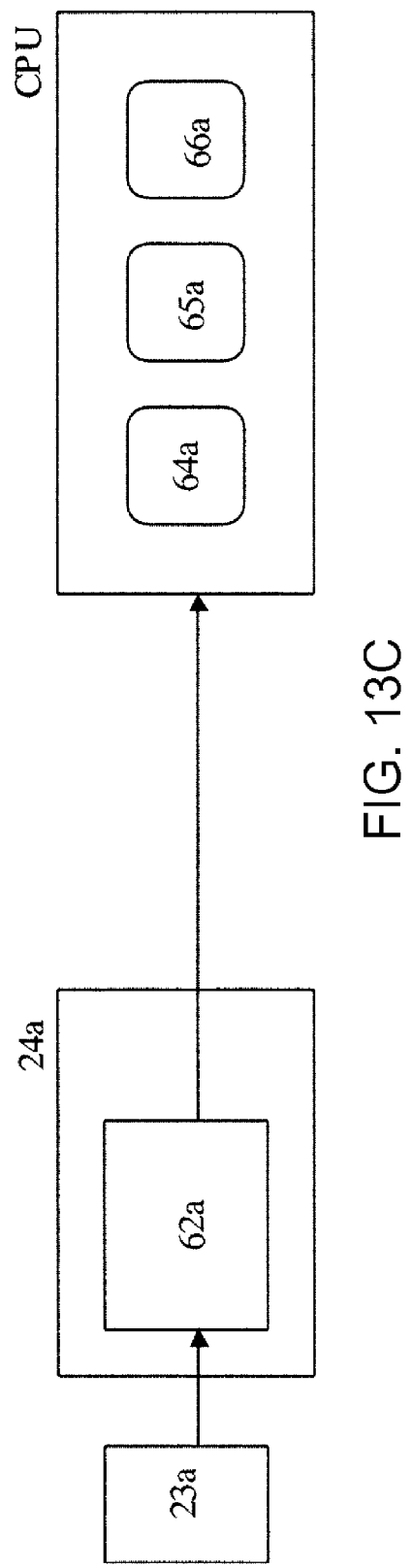
FIG. 13C is a diagram depicting a configuration of a constrained power calculating circuit of Example 3.

FIG. 13A shows an example of the CPU sharing only the LOG conversion processing 66a, FIG. 13B shows an example of the CPU sharing the product sum calculation 65a and the LOG conversion 66a, and FIG. 13C shows an example of the CPU sharing all the calculations in the backward substitution 64a and later stages. In these examples, the CPU shares a part of the constrained minimum power calculation, but most of the calculation volume of the constrained minimum power calculation is that of the QR decomposition calculation 62a. In order to execute the QR decomposition calculation 62a at high-speed, it is important to calculate a plurality of correlation matrices in parallel, as the present invention discloses. If a part of the processing of which calculation volume is low is executed by software processing in the CPU, a circuit resource can be allocated to the processing of which calculation volume is high, and the processing speed can be increased.

Example 4

Figure 14:
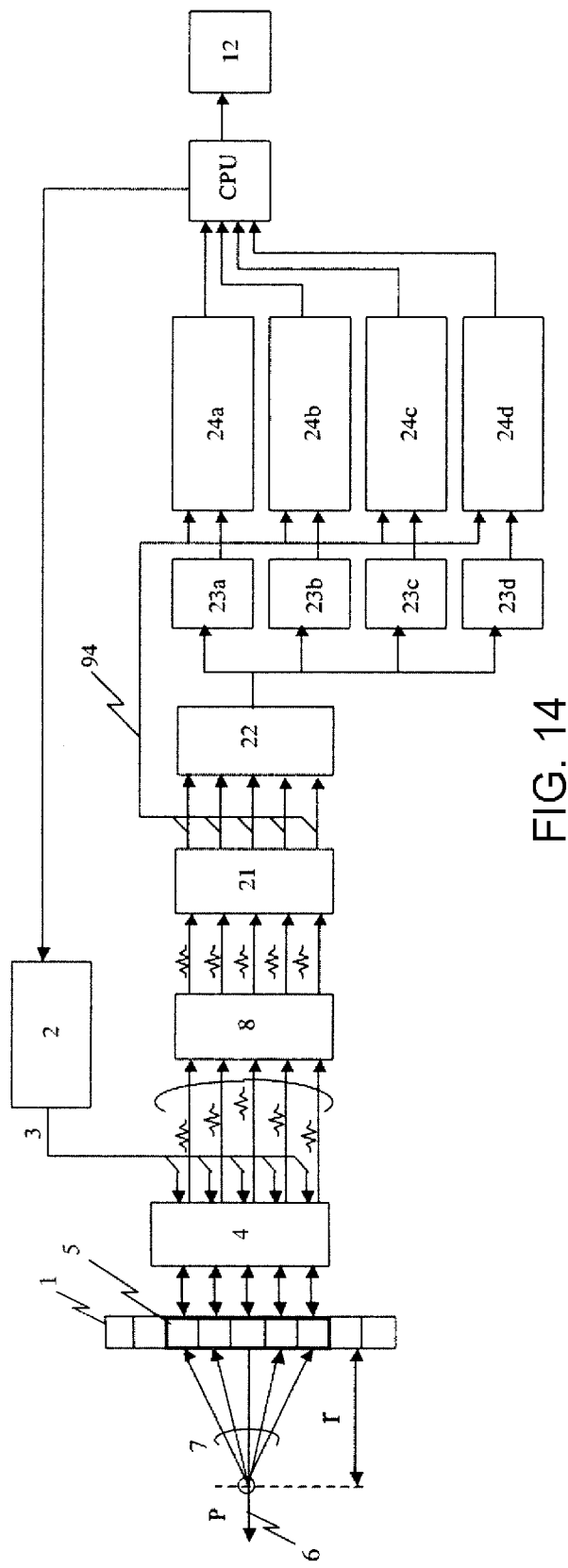
FIG. 14 is a diagram depicting a configuration of an acoustic wave imaging apparatus of Example 4.

In this example, a case in which the calculation procedure of the constrained minimum power is different from the above examples will be described. FIG. 14 shows an example of an apparatus which does not calculate the constrained minimum power directly by Expression (8), but calculates an optimum weight vector $W_{min}$ first using Expression (7), then calculates the constrained minimum power as an inner product of the calculated weight vector $W_{min}$ and an input signal vector X. In this case, complex input signals 94, which are output from complex signal acquiring circuits 21, are input to each constrained electric power calculating circuit, since the constrained power calculating circuits 24a, 24b, . . . calculate the inner products of an optimum weight vector $W_{min}$ and the complex input signals.

Figure 15:
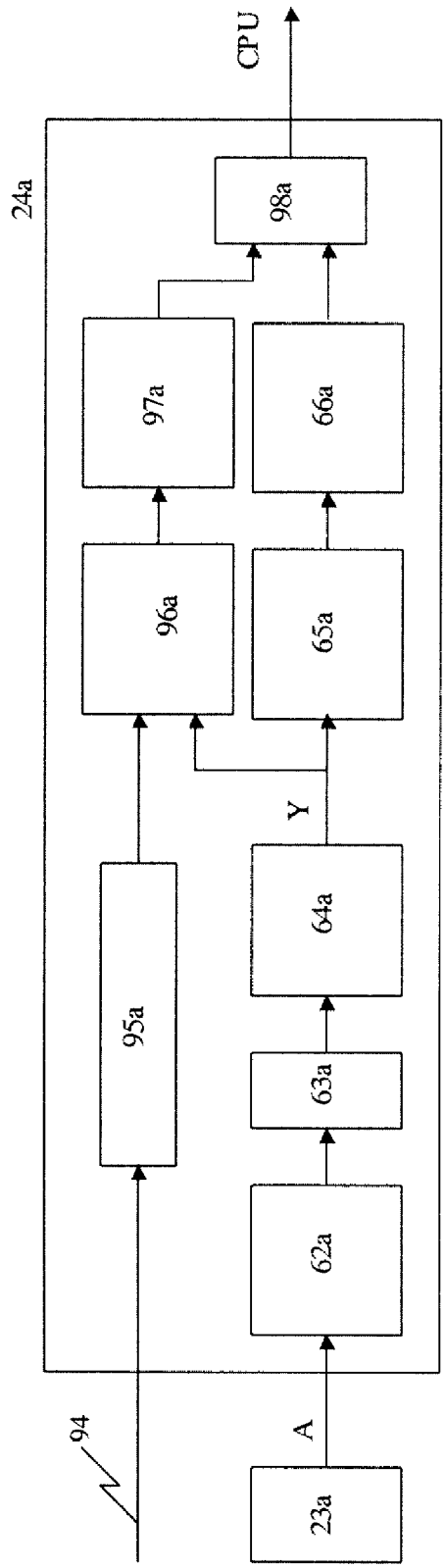
FIG. 15 is a diagram depicting a configuration of a constrained power calculating circuit of Example 4.

FIG. 15 is a diagram depicting a concrete configuration of the constrained electric power calculating circuit 24a of this example. In FIG. 15, the backward substitution calculating circuit 64a outputs the solution Y of the simultaneous linear equations (9), and is given by Expression (14):

[Math. 14]

$$Y = A^{-1}C \quad (14)$$

Therefore, if the product sum calculating circuit 96a could calculate the inner product of the complex input signal (X) 94, of which time was adjusted by the delay circuit 95a, and Y, as shown in FIG. 15, then the numerator of Expression (15), which is an expression to calculate the constrained minimum power, can be calculated:

[Math. 15]

$$X^H W_{min} = \frac{X^H A^{-1} C}{C^H A^{-1} C}. \quad (15)$$

Since the denominator of Expression (15) is calculated by the product sum calculation circuit 65a, the LOG conversion value of the constrained minimum power of Expression (15) can be calculated by the LOG conversion circuits 97a and 66a performing LOG conversion on the numerator and the denominator respectively, and the difference circuit 98a determining a difference of the respective results. By means of this operation, the constrained minimum power at each timing can be calculated at a cycle faster than the cycle of calculating the correlation matrix, and as a result, the resolution of an output echo image can be improved.

Example 5

Figure 16:
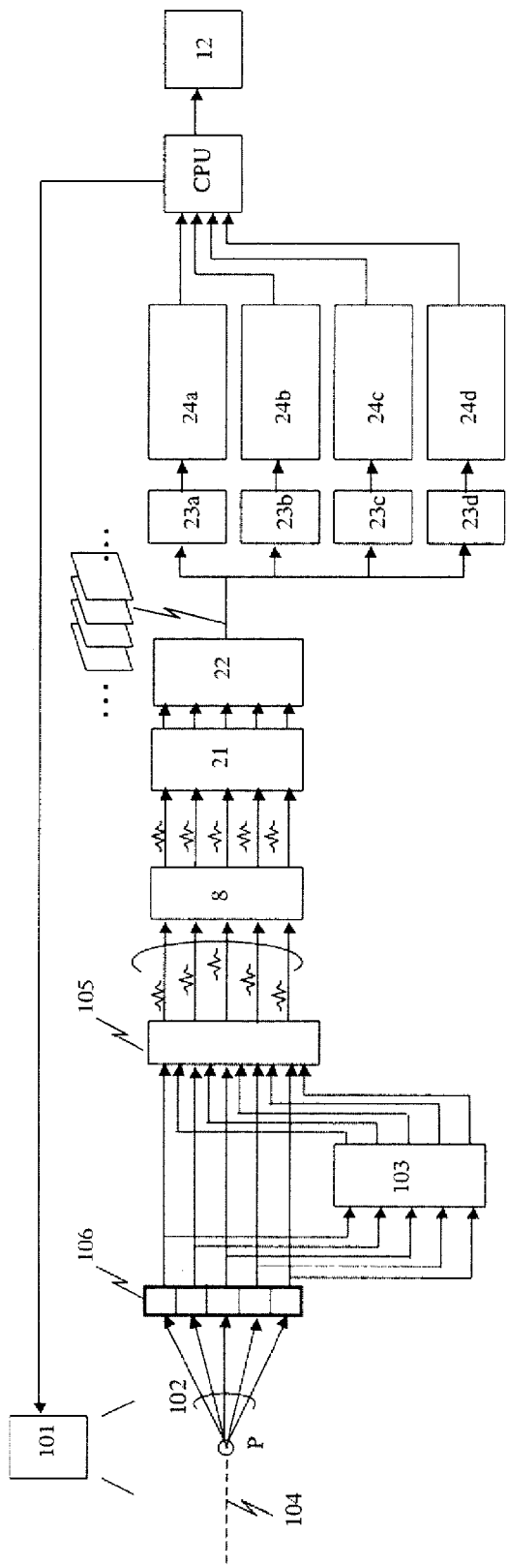
FIG. 16 is a diagram depicting a configuration of a photoacoustic wave imaging apparatus of Example 5.

In this example, a case of an acoustic wave imaging apparatus in which the acoustic wave to be received is a photoacoustic wave, will be described. FIG. 16 is an example of a photoacoustic imaging apparatus in which the CMP method is applied to the processing of photoacoustic signals. In FIG. 16, a light source 101 irradiates the interior of an object with an electromagnetic wave based on an instruction from the CPU. Each inspection target substance existing in the object absorbs the irradiated electromagnetic wave, and simultaneously generates photoacoustic waves by thermal expansion. An acoustic wave receiving element group 106 converts the arrived acoustic waves into electric signals, and transmits the electric signals to a phase aligning delay circuit 8 via a selection circuit 105.

Here if an arbitrary scanning line 104 is defined inside the object, and only a photoacoustic wave generated on the scanning line 104 is focused on, a generation position P of the photoacoustic wave 102, to be received by the acoustic wave receiving element group 106, moves as time elapses, from a close position to a distant position on the scanning line 104. Hence if a delay time in the phase aligning delay circuit 8 is appropriately changed according to the receive time, then the phase aligning delay circuit 8 can output the photoacoustic wave signals generated at all the points on one scanning line 104 as phase-aligned signals.

These signals are exactly the same as the signals generated by performing the phase aligning delay operation on echo signals obtained by transmitting an acoustic wave beam in the scanning line 104 direction, and therefore a photoacoustic signal intensity waveform can be calculated based on the CMP method, using the circuit configuration in FIG. 16, which is exactly the same as that in the case of receiving echo signals. As a consequence a photoacoustic image of the entire surface inside the object can be generated by repeating irradiation of the electromagnetic waves and reception of the photoacoustic waves, while moving the position of the scanning line.

It is also possible to dispose a storage circuit 103 for storing received signals as shown in FIG. 16, so that the received signals by the first electromagnetic wave irradiation are stored in the storage circuit 103, and signals read from the storage circuit 103 are used as the received signals for the second or later electromagnetic wave irradiation. By means of this configuration, the number of times of electromagnetic wave irradiation required to obtain the desired information can be dramatically decreased, since the same received signals are used every time as long as the positions of the light source 101 and the acoustic wave receiving element group 106 are unchanged, and as a result, an efficient apparatus can be implemented.

The present invention is based on the assumption that the constrained minimum power values defined by Expression (1) to Expression (8) are calculated, but exactly the same calculation can be performed, for example, by performing linear conversion on n received signals, and using these signals as newly received signals. According to the present invention, even if various modifications are performed on the received signals, the power P can be defined as a quadratic form based on Hermitian matrix A, using the form of Expression (16) or similar form which does not affect the calculation result:

[Math. 16]
$$P = W^H A W \quad (16)$$

The present invention is applicable just the same for any problem to determine a solution to minimize the electric power given by Expression (16) under the constraint given by Expression (6).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-091290, filed on Apr. 12, 2010, which is hereby incorporated by reference herein in its entirety.

The invention claimed is:

1. An acoustic wave imaging apparatus, comprising:
a plurality of acoustic wave receiving elements each receiving an acoustic wave emitted from an object, and converting the acoustic wave into a received signal;
a phase aligning unit which aligns phases of a plurality of received signals obtained from said plurality of acoustic wave receiving elements;
a complex signal acquiring unit which generates complex signals out of the phase-aligned received signals obtained by said phase aligning unit and acquires a plurality of complex signals;
a correlation matrix calculating unit which calculates a correlation matrix of the plurality of complex signals; and
an electric power calculating unit which calculates constrained minimum power of the received signals, using the correlation matrix and a predetermined constraint vector,
wherein
said correlation matrix calculating unit calculates the correlation matrix at a predetermined cycle, and sequentially outputs the calculated correlation matrix to said electric power calculating unit, and
said electric power calculating unit comprises a plurality of storage circuits and a plurality of power calculating circuits, wherein said plurality of power calculating circuits correspond to said plurality of storage circuits respectively, and pairs of one of said storage circuits and one of said power calculating circuits are arranged in parallel with each other, and
said storage circuits sequentially and cyclically store the correlation matrix data input from said correlation matrix calculating unit, and
said power calculating circuit calculates a constrained minimum power by use of the correlation matrix input from said correlation matrix calculating unit to the corresponding one of said storage circuits, and outputs the result, while the next correlation matrix is input to the same corresponding storage circuit.

2. The acoustic wave imaging apparatus according to claim 1, wherein $N >= Tp/Tm$ is established, where Tm is a cycle of said correlation matrix calculating unit calculating the correlation matrix, Tp is a time from when said electric power calculating unit receives input of the correlation matrix to when said electric power calculating unit calculates constrained minimum power and outputs this power, and N is the number of the plurality of constrained minimum powers which said electric power calculating unit calculates in parallel.

3. The acoustic wave imaging apparatus according to claim 1, wherein said correlation matrix calculating unit calculates the correlation matrix at a 5 MHz or higher cycle.

4. The acoustic wave imaging apparatus according to claim 1, wherein said electric power calculating unit performs QR decomposition processing and backward substitution processing when the constrained minimum power is calculated.

5. The acoustic wave imaging apparatus according to claim 4, wherein said electric power calculating unit executes at least the QR decomposition processing by using a digital circuit.

6. The acoustic wave imaging apparatus according to claim 4, wherein said electric power calculating unit executes at least one of the QR decomposition processing and the backward substitution processing by using a pipeline type circuit.

7. The acoustic wave imaging apparatus according to claim 1, wherein said electric power calculating unit determines weight vectors, which are applied to the plurality of complex signals respectively, based on the correlation matrix and a predetermined constraint vector, and calculates the constrained minimum power of the received signals.

8. The acoustic wave imaging apparatus according to claim 1, wherein the acoustic wave is an acoustic wave which is transmitted by the acoustic wave receiving element, and is reflected inside the object.

9. The acoustic wave imaging apparatus according to claim 1, wherein the acoustic wave is a photoacoustic wave generated when the object absorbs light irradiated from a light source.

* * * * *